(12) United States Patent
Elkind et al.

(10) Patent No.: US 6,326,612 B1
(45) Date of Patent: Dec. 4, 2001

(54) SYSTEM AND METHOD FOR OPTICAL SENSING UTILIZING A PORTABLE, DETACHABLE SENSOR CARTRIDGE

(75) Inventors: Jerome L. Elkind, Richardson; Richard A. Carr, Rowlett; Jose L. Melendez, Plano, all of TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 09/416,560

(22) Filed: Oct. 12, 1999

Related U.S. Application Data

(60) Provisional application No. 60/104,043, filed on Oct. 13, 1998.

(51) Int. Cl.$^7$ .................................................. G01N 21/00
(52) U.S. Cl. ...................... 250/239; 250/573; 422/82.05; 436/165
(58) Field of Search ............................ 250/239, 227.11, 250/227.14, 227.24, 227.25, 573, 574, 575, 576, 577; 422/91, 82.05, 82.06, 82.07, 82.08, 82.09, 82.11, 82.12, 58; 436/165; 356/73, 39, 40, 41, 42; 600/308; 204/411; 205/782

(56) References Cited

U.S. PATENT DOCUMENTS

| | | | |
|---|---|---|---|
| 5,313,264 | * | 5/1994 | Ivarsson et al. ....................... 356/73 |
| 5,325,853 | * | 7/1994 | Morris et al. ........................ 600/308 |
| 5,405,510 | * | 4/1995 | Betts et al. ........................... 205/782 |
| 5,922,285 | * | 7/1999 | Melendez et al. ................. 422/82.08 |
| 5,946,083 | * | 8/1999 | Melendez et al. ..................... 356/73 |
| 6,024,923 | * | 2/2000 | Melendez et al. ................. 422/82.08 |
| 6,123,820 | * | 9/2000 | Bergkuist et al. .................... 204/411 |

* cited by examiner

Primary Examiner—John R. Lee
(74) Attorney, Agent, or Firm—W. James Brady, III; Frederick J. Telecky, Jr.

(57) ABSTRACT

Disclosed is a sensing system and method utilizing a sensor cartridge (10) for making analytical measurements regarding one or more samples (50) of interest, the cartridge (10) comprising an opaque housing (12) having an opening (32), the opening (32) allowing access to one or more electrically conductive contacts (34) and one or more fluidic connectors (36) disposed within the housing (12) and mechanically aligned to the electrically conductive contacts (34), a flow cell (56) having one or more channels connected to the one or more fluidic connectors (36), and a fixed optic sensor (68, 58, 72, 74) disposed within said housing (12) and aligned to a sensing surface on the flow cell. The fixed optic sensor may be, for example, a surface plasmon resonance sensor, a critical angle sensor, or a fluorescence-based sensor. In one embodiment of the present invention, the one or more electrically conductive contacts (32) comprise card-edge contacts (34). In an alternative embodiment of the present invention, the one or more electrically conductive contacts comprise conductive pins (124) intended to be inserted into a socket (128) of a reporter unit (130). Because the optic sensor is pre-aligned, e.g., a sensing surface portion of the optic sensor is mounted on the flow cell, and at least one of the fluid connectors is aligned to the electrical contacts, the cartridge can be easily replaced on a host unit to allow, e.g., field analysis of multiple fluids.

22 Claims, 4 Drawing Sheets

SYSTEM AND METHOD FOR OPTICAL SENSING UTILIZING A PORTABLE, DETACHABLE SENSOR CARTRIDGE

This application claims priority under 35 USC § 119(e)(1) of provisional application number 60/104,043 filed Oct. 13, 1998.

FIELD OF THE INVENTION

The present invention relates in general to sensor systems in the fields of chemical, biochemical, biological and biomedical analysis, and more particularly, to a system and method for optical sensing utilizing a portable, detachable sensor cartridge device for permitting qualitative and quantitative analysis about a sample of interest when used in conjunction with a fixed optic sensor.

BACKGROUND OF THE INVENTION

Without limiting the scope of the invention, its background is described in connection with analytical measurements of a wide variety of analytes using a fixed optic sensor employed in sensor systems in the fields of chemical, biochemical, biological and biomedical analysis, such as a surface plasmon resonance sensor, a critical angle sensor, or a fluorescence-based sensor, for example.

Summarized briefly, a surface plasmon is known in the art as a surface charge density wave at the surface of a dielectric interface having a thin conductive film formed thereon. The oscillation of free electrons at a conductor-dielectric boundary is affected by the refractive index of the material adjacent to the film. Using a polarized beam of monochromatic light, surface plasmon polaritons can be excited. Resonance occurs when the polarized light is totally internally reflected from the conductive film. The light internally reflected from the film has a minimum intensity at the resonance angle. By detecting the resonance angle, the refractive index of a material adjacent to the film may be determined, which is indicative of other properties of the material. A more detailed description of surface plasmon resonance may be found in the article "Surface Plasma Oscillations and Their Applications," Rather, H., *Physics of Thin Films*, 1977.

Sensing systems using critical angle measurements are also known in the art. Since critical angle is a mathematical function of refractive index, determination of the critical angle gives rise to the determination of the refractive index of a sample, which is indicative of one or more sample properties, from which further qualitative and quantitative analyses about the sample may be made. In a typical critical angle sensor system, when polarized light rays are directed to a sample of interest at angles of incidence smaller than the critical angle, a portion of the light is refracted into the sample, resulting in an overall loss. At angles of incidence larger than the critical angle, total internal reflection occurs, and the full intensity of the light is reflected off the sample. The critical angle, and consequently the refractive index, may be then determined by measuring the intensities of the reflected light rays, and detecting a transition from a high intensity to a low intensity. A more detailed description of critical angle sensors may be found in U.S. patent application Ser. No. 60/027,286, the contents of which are herein incorporated by reference.

The use of fluorescence based methodologies to detect sample gases and liquids is also known in the prior art. A typical application involves the molecular labeling of a film or other article followed by excitation and fluorescent measurement in the presence of the particular sample of interest. Fluorescent labeling involves the deposit of a suitable fluorescence chemistry known to interact with the sample of interest. A source of excitation light is directed at the coated article, which when brought in contact with the sample, emits a low intensity fluorescence energy. A photodetector may be used to measure the emission and therefore detect the presence of the sample. A more detailed description of fluorescence-based sensors may be found in U.S. patent application Ser. No. 60/027,287, the contents of which are herein incorporated by reference.

SUMMARY OF THE INVENTION

In prior art sensing systems, analytical measurements have been primarily conducted in a centralized testing environment. This generally requires that a sample of interest be brought to a specially equipped lab for analysis. Such a testing environment restricts measurements to those that can tolerate delays effected by, as well as costs imposed by such a methodology. As often is the case with the use of biomedical sensors in medical emergencies, for example, analytical determinations must be immediately made in-situ.

Furthermore, in prior art sensing methodologies, optical connections, fluidic connections and electrical connections to a host unit have been usually made in a series of steps. Typically, a sensor is first plugged into its electrical socket, and subsequently, an inlet tube is inserted into a flow cell. Optical connections are then achieved, and precise optical alignment and calibration are made. Such a methodology is time-consuming and difficult and does not generally allow for analytical measurements to be taken easily, rapidly and accurately at the point of need.

Furthermore, sensors in the prior art have typically utilized metal pins as electrical connectors to a host unit. These pins are typically exposed and are therefore more susceptible to damage such as electrostatic interference or shorting. These unprotected pins are even more susceptible to damage if the sensing device has a slick surface, making it more slippery and therefore more likely to be dropped.

Yet another problem with prior art sensing systems involves the generation of biohazardous waste. The potentially contagious nature of this waste dictates that it be collected efficiently and disposed of properly.

A need has therefore arisen for an efficient, portable, replaceable sensing device that overcomes the disadvantages in the prior art. A sensing device that can perform measurements at the point of need and that simultaneously and rapidly provides for fluidic connections and electrical connections while eliminating the need for separate optical connections would be extremely advantageous over the prior art. A device that is small, portable, and lightweight, and that integrates the electrical and fluidic connectors and the various electro-optical sensing components on a single platform would have widespread application and would fill the void left by prior art sensors. A device that is low-cost, and allows for efficient, high-volume, wafer-scale mass production would be highly desirable as well.

The present invention disclosed herein can comprise an optical sensing system and sensor cartridge for making analytical measurements regarding one or more samples of interest, the cartridge comprising an opaque housing having an opening, the opening allowing access to one or more electrically conductive contacts and one or more fluidic connectors disposed within the housing; a flow cell having one or more channels connected to the one or more fluidic connectors; and a fixed optic sensor disposed within the housing. The fixed optic sensor system may be, for example, a surface plasmon resonance sensor, a critical angle sensor, or a fluorescence-based sensor. In one embodiment of the present invention, the one or more electrically conductive contacts comprise card-edge contacts. In an alternative embodiment of the present invention, the one or more electrically conductive contacts comprise conductive pins intended to be inserted into a socket of a host analytical unit.

Because the optic sensor is pre-aligned, e.g., a sensing surface portion of the optic sensor is mounted on the flow cell, and at least one of the fluid connectors is aligned with the electrical contacts, the cartridge can be easily replaced on a host unit to allow, e.g., field analysis of multiple fluids.

The present invention can provide a sensing device that simultaneously and rapidly provides for both fluidic connections and electrical connections and thus can provide meaningful data to be analyzed and interpreted by a host unit such as a computer or other similar system.

The present invention can also provide a low cost sensor that may be manufactured in high volume. The present invention can be a miniature, lightweight, portable, detachable sensor that uses low-cost components which, in one embodiment of the invention, may be integrated onto a single platform.

It can be seen that cleaning of such flow cell between tests, while practical in laboratory environments, is not generally practical in field situations. It can also be seen that carrying entire multiple analysis systems around in the field is also generally impractical. By providing for detachable, replaceable cartridges with the flow cell pre-aligned to at least one electrical sensor, the system described herein with aligned fluidic and electrical connectors makes multiple tests possible in a portable system.

For a more complete understanding of the present invention, including its features and advantages, reference is now made to the following detailed description, taken in conjunction with the accompanying drawings.

BRIEF DESCRIPTION OF THE DRAWINGS In the drawings.

Corresponding numerals and symbols in the different figures refer to corresponding parts unless otherwise indicated.

DETAILED DESCRIPTION OF THE PREFERRED EMBODIMENT

Figure 1:
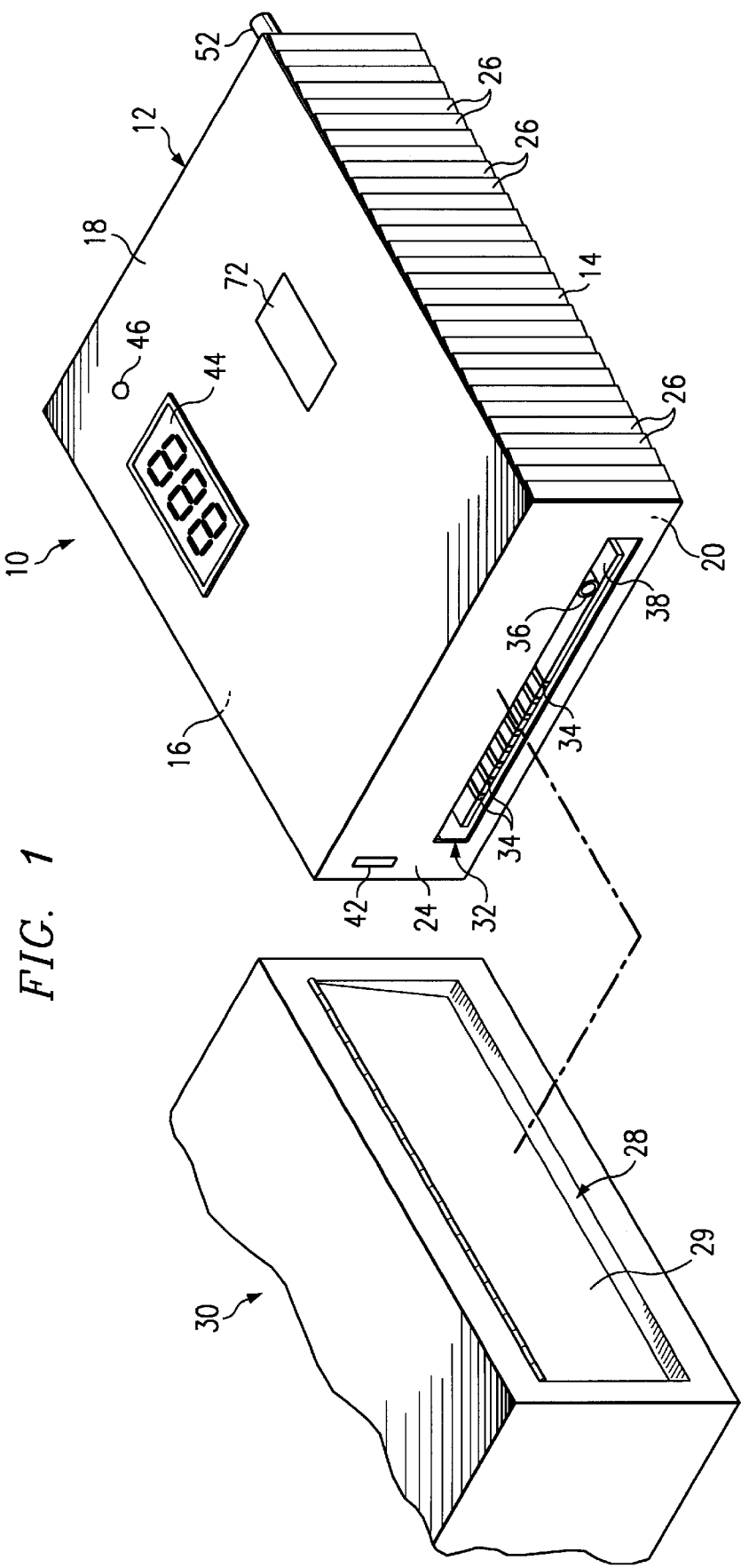
FIG. 1 depicts a perspective view of a sensing system with a sensing cartridge in accordance with the present invention.
Figure 2:
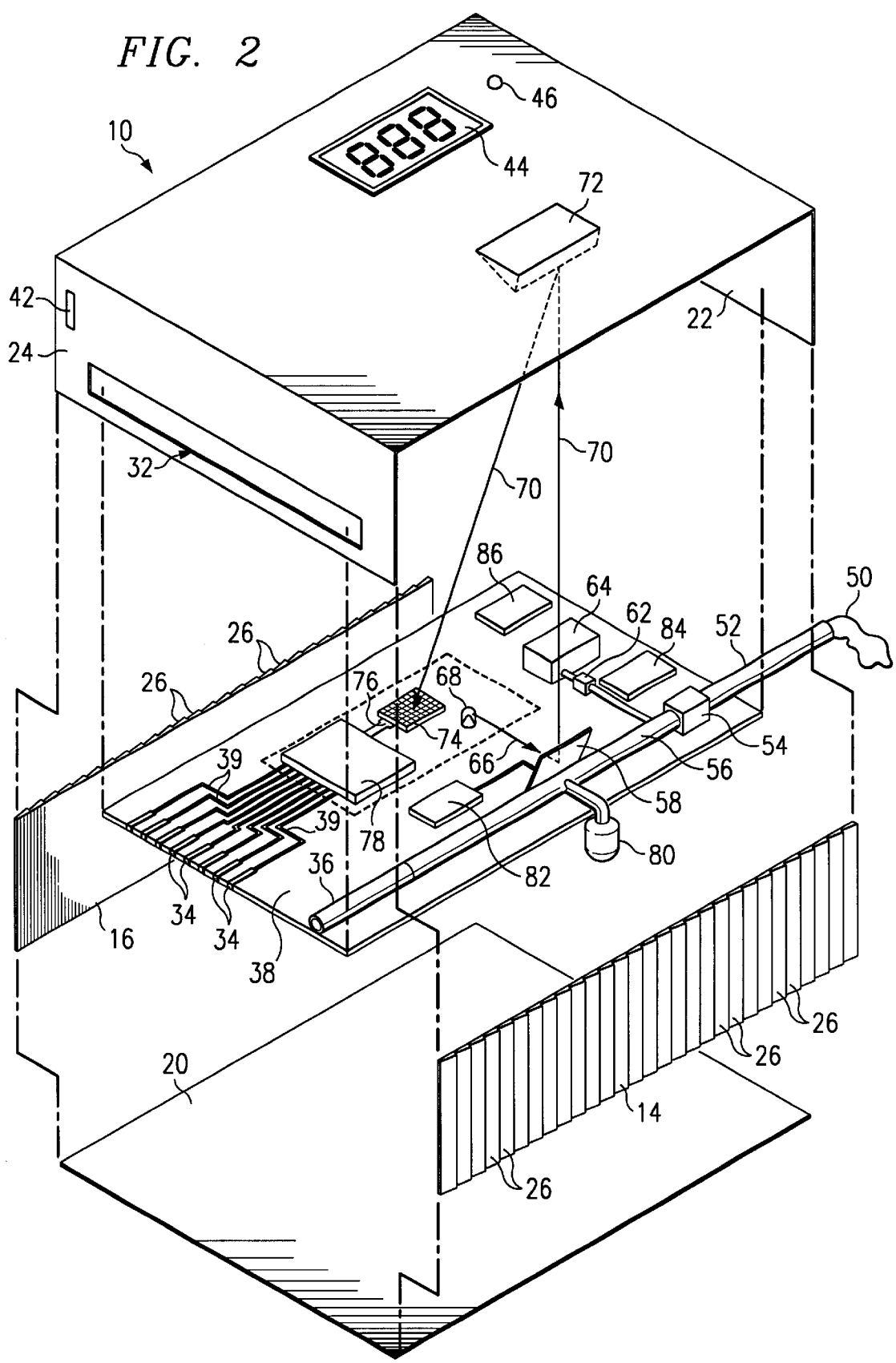
FIG. 2 depicts a exploded perspective view of the sensing cartridge of FIG. 1.

The advantages of the present invention are made readily apparent to those skilled in the art as shown in FIGS. 1 and 2. A cartridge sensing device is shown in FIG. 1 and generally depicted as 10. As shown in FIG. 2, the various components of sensing device 10 are disposed within a housing 12. Housing 12 is shown as having walls 14, 16, 18, 20, 22 and 24 for providing mechanical support for the components contained therein. Housing 12 is composed of a black or otherwise opaque material suitable for blocking the entry of ambient light.

In one embodiment of the present invention, one or more of walls 14, 16, 18, 20, 22 and 24 may have contours 26 for creating a textured surface to facilitate secure holding and gripping of sensing device 10 and prevent dropping of sensing device 10. For example, as shown in FIGS. 1 and 2, walls 14 and 16 may have a ribbed texture. Furthermore, walls 14 and 16 may have depressions or protrusions (not shown) that facilitate extraction of sensing device 10 from a port 28 of an analytical unit 30. Those skilled in the art should readily appreciate that while housing 12 is depicted in FIGS. 1 and 2 as having six rectangular walls 14, 16, 18, 20, 22, and 24, various other geometrical configurations of housing 12 are within the scope of the present invention. For example, one or more of walls 14, 16, 18, 20, 22 and 24 may be trapezoidal or curved.

Wall 24 has an opening 32 to enable simultaneous mating of one or more electrical connectors 34 and one or more fluidic connectors 36, which are shown as substantially parallel, with corresponding connectors (not shown) of a host analytical unit 30. Host analytical unit 30 may have an opening 28 covered by a flap 29 to protect the connectors to one or more electrical connectors 34 and one or more fluidic connectors 36. Host analytical unit 30 is an external system, and may be used in conjunction with another analytical device such as a computer, hand-held meter, calculator, printer, reporter unit, logic analyzer, oscilloscope, or other similar analytical tool or system.

Electrical connectors 34 are preferably card-edge conductive leads affixed to a platform 38 such as a printed circuit board (PCB) and are further connected to other components within housing 12 via electrically conductive paths 39. Fluidic connectors 36 may be composed of teflon or other suitable material that is chemically inert with respect to samples likely to be used with sensing device 10. Platform 38 may be recessed from the surface of wall 24 to protect electrical connectors 34 and fluidic connectors 36 from external elements and from damage to electrical connectors 34 and fluidic connectors 36 resulting from mis-handling or dropping sensing device 10.

Additionally, opening 32 of wall 24 may be covered by a protective lid (not shown). The lid functions to keep dust and other undesired particulate matter from entering housing 12, thereby protecting the integrity of electrical connectors 34 and fluidic connectors 36. The lid may be retractable or otherwise removable.

Wall 24 may have an orientation guide 42 to facilitate aligning sensing device 10 with host analytical unit 30, thereby ensuring proper connection of electrical connectors 34 and fluidic connectors 36 with their respective mating connectors disposed in host analytical unit 30. Sensing device 10 may also have an indicator 46, such as a light emitting diode (LED), for example, which turns on if the electrical connection between sensing device 10 and host analytical unit 30 is determined to be appropriate. Furthermore, sensing device 10 may have a display 44 indicative of the desired application of sensing device 10. Display 44 may be a clearly visible printed label affixed to the outside of housing 12 having alphanumeric characters, colors, symbols, or various other elements, or display 44 may be a liquid crystal display (LCD) or other electronic display.

Operation of sensing device 10 commences with simultaneous mating of electrical connectors 34 and fluidic connectors 36 of sensing device 10 with their respective connectors disposed in host analytical unit 30. Fluidic connection may be achieved by a teflon-to-teflon slip fit connection. Electrical connection may be accomplished by direct contact between electrical connectors 34 of sensing device 10 and electrical contacts of host analytical unit 30.

In accordance with the present invention, once such electrical and fluidic connections are established, a sample 50 is drawn into sensing device 10, utilizing appropriate valving to a vacuum pump contained within host analytical unit 30. Sample 50 is generally fluidic matter having one or more properties which are desired to be determined for chemical, biochemical, biological or biomedical analysis. Sample 50 enters sensing device 10 via one or more inlets 52. Sample 50 may pass through one or more filters 54 in order to prevent undesired particulate matter from interfering with measurement of its desired properties. Sample 50 proceeds into a flow cell 56, which is generally a cell composed of teflon or other suitable inert material, and having a hollowed portion functioning as a channel through which sample 50 is guided.

After sample 50 is drawn into sensor device 10, sample 50 may be brought into contact utilizing an appropriate valve 62, with one or more materials stored in one or more reservoirs 64. These materials may include without limitation materials used for calibration purposes, cleaning purposes, or reagents or reactants intended to react with sample 50.

Sample 50 proceeds through flow cell 56 across a sensing surface 58. Sensing surface 58 may comprise a slide composed of glass, plastic, or other optically suitable material, and having a thin coating. The composition of the coating is determined by the desired function of sensing device 10 and may be tailored accordingly.

In accordance with surface plasmon resonance sensing systems, for example, light rays 66 emanating from a polarized monochromatic light source 68 hit sensing surface 58. Sensing surface 58 is generally in contact with sample 50 and is shown enlarged in FIG. 2 for ease of illustration. The reflective components 70 of light rays 66 are reflected from sensing surface 58 onto reflective surface 72, and are then reflected from reflective surface 72 onto a photodetector array 74. Reflective surface 72 may be flat, or may be concave or convex. Thus, light source 68, sensing surface 58, reflective surface 72, and photodetector array 78 provide a fixed optic sensor in this embodiment.

For optical radiation, a suitable photodetector array 74 has an array of discrete photosensing areas, or pixels. Light energy striking a pixel generates electron-hole pairs in the region under the pixel. The field generated by the bias on the pixel causes the electrons to collect in the element while the holes are swept into the substrate. Each sensing area in photodetector array 74 thereby produces a signal on an output with a voltage that is proportional to the intensity of the light striking that area of photodetector array 74. This intensity and its corresponding voltage are at their maxima in the total internal reflection region.

The output, representing bit level data from the photodetector array 74, is transmitted via interface 76 to a digital signal processing (DSP) unit 78 for further qualitative and/or quantitative analysis. Digital signal processing unit 78 may provide interface control signals, such as clock line and serial input, for protocol communications with photodetector array 74. Output signals from signal processing unit 78 are transmitted to electrical contacts 34 via conductive paths 39.

Finally, sample 50 is captured in a waste unit 80 in lieu of proceeding into host analytical unit 30 via fluidic connectors 36. Waste unit 80 may comprise a receptacle for storing sample 50, or alternatively, a membrane or sponge for absorbing sample 50. Indicator 46 may be connected to a level detector or other sensing device connected to waste unit 80 such that when waste unit 80 is at full capacity, indicator 46 turns off. Sensing device 10 may be disposed of when waste unit 80 is full, and may be replaced by another sensing device. While the above description has been offered with respect to one sample 50, those skilled in the art should readily understand that other configurations are possible that utilize valves for more dynamic sampling, and additional samples may be drawn simultaneously utilizing a plurality of inlets 54.

In addition, sensing device 10 may further comprise a thermistor 82 or other temperature sensing device to ensure that the temperature within housing 12 is consistent for optimal performance. Sensing device 10 may additionally comprise a thermal heat generating device 84, such as a heating coil, for example. Sensing device 10 may further comprise a thermal heat exchange device 86, such as fan, for example. Thermal heat generating device 84 and thermal heat exchange device 86 would function to stabilize the temperature within housing 12.

Those of skill in the art will recognize that the elements of sensor device 10 can be relocated, rearranged or reoriented within housing 12 while retaining equivalence in function according to the present invention.

Figure 3:
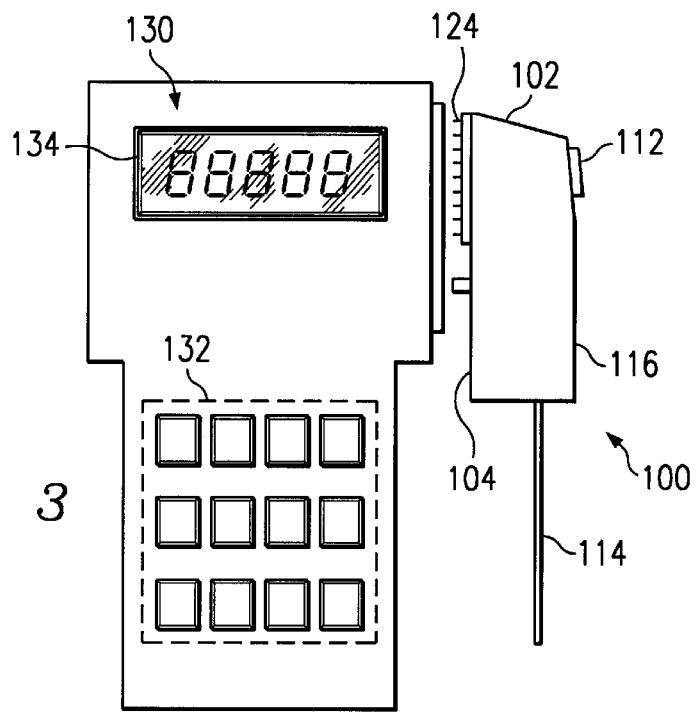
FIG. 3 depicts a top view of an alternative embodiment of a sensing system with a sensing cartridge in accordance with the present invention.
Figure 4:
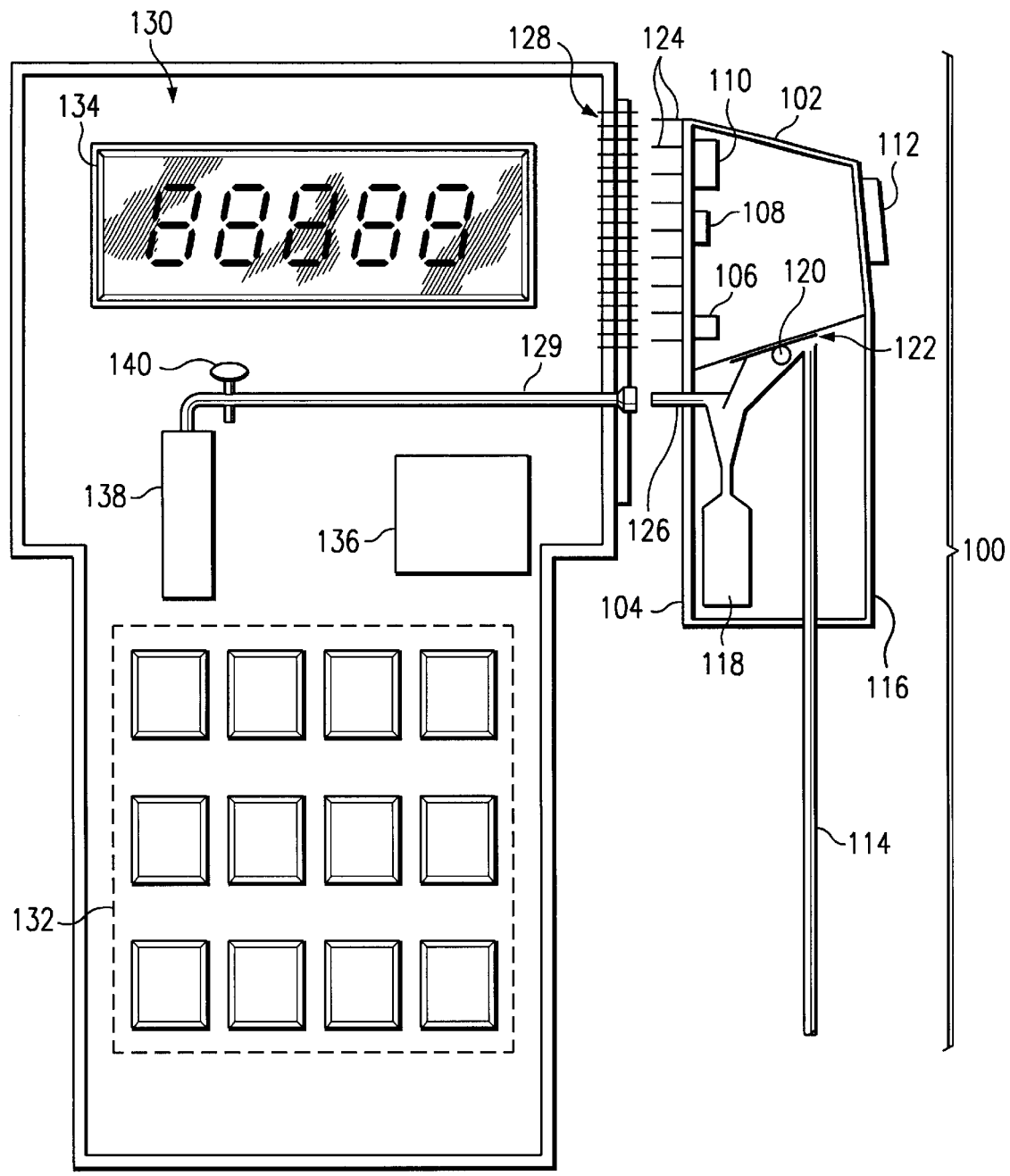
FIG. 4 depicts cross-sectional view of the sensing system with a sensing cartridge of FIG. 4.

Reference is now made to FIGS. 3 and 4, in which an alternative embodiment of the present invention is depicted. Sensing device 100 comprises a housing 102, with the following components enclosed therein: a platform 104, an LED 106, a memory array 108, a photodetector array 110, a mirrored surface 112, an inlet 114, a flow cell 116, a waste receptacle 118, a thermistor 120, a sensor surface 122, a plurality of conductive pins 124, and a fluidic connector 126. In the alternative embodiment depicted in FIGS. 3 and 4, electrical connection may be achieved by insertion of conductive pins 124 of sensing device 100 into a socket 128 of a reporter unit 130, such as a socket with snug-fit receptors or a textool or other zero insertion force (ZIF) socket. Conductive pins 124 and fluidic connector 126 are simultaneously inserted into socket 128 and fluidic tube 129, respectively, of reporter unit 130. Socket 128 can be modified to provide a feed through for fluidic connections that are parallel to the conductive pins 124. Reporter unit 130 comprises socket 128 and fluidic tube 129, a keypad 132, a display 134, a digital signal processing unit 136, a pump 138, and a valve 140. Reporter unit may also have a protective flap (not shown) to protect the integrity of socket 128 and fluidic tube 129.

Those of skill in the art will recognize that the elements of sensor device 100 can be relocated, rearranged or reoriented within housing 102 while retaining equivalence in function according to the present invention.

Figure 5:
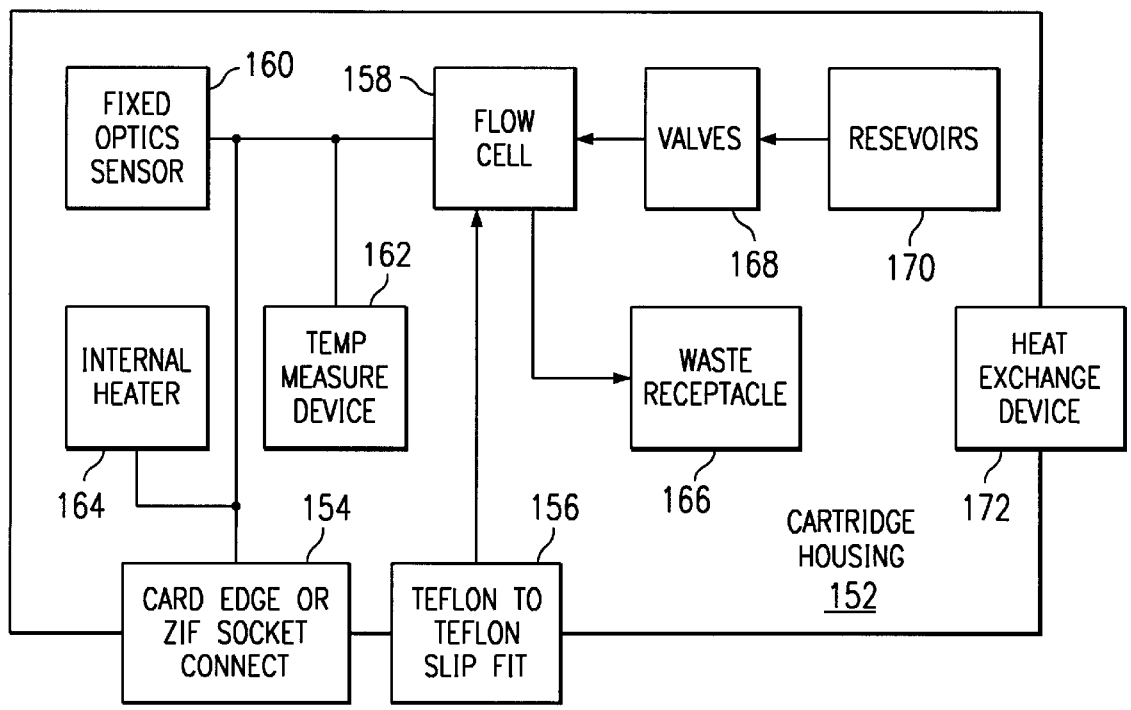
FIG. 5 depicts a block diagram of an embodiment of a sensing cartridge in accordance with the present invention.

Reference is now made to FIG. 5 in which a block diagram of an embodiment of a cartridge sensing device in accordance with the present invention is generally depicted as 150. Sensing device 150 comprises a housing 152, a means for electrical connection 154, a means for fluidic connection 156, a flow cell 158, a fixed optic sensor 160, a temperature measuring device 162, a heater 164, one or more waste receptacles 166, one or more valves 168, one or more reservoirs 170, and a heat exchange device 172.

Housing 152 may be black or otherwise substantially opaque in order to block ambient light. Means for electrical connection 154 may comprise a card edge connector or a connector for insertion into a socket such as a ZIF socket. Means for fluidic connection 156 may comprise a teflon to teflon slip fit connector that can be connected to or disconnected from a host unit very easily, quickly, and repeatedly.

Temperature measuring device 162 monitors the temperature within the cartridge. Heater 164 and heat exchange device 172 ensure that the temperature within sensing device 150 is acceptable for optimal performance.

Flow cell 158 may comprise a liquid inlet directed appropriately for sampling to take place, and an outlet that may be connected directly or though appropriate valving to a vacuum pump, contained within a host unit (not shown). A liquid sample may therefore be pulled into sensing device 150, and guided across a sensing surface of fixed optics sensor 160 for analysis in accordance with fixed optic sensing technologies. Rather than proceeding into the pump, the liquid is caught in one or more waste receptacles 166 that are also contained in cartridge 152. Other sensing system configurations according to the present invention may utilize one or more valves 168 for dynamic sampling, including applying one or more reagents contained in one or more reservoirs 170. One or more reservoirs 170 may also contain cleaning solutions or materials for calibration purposes.

Those of skill in the art will recognize that the elements of sensing device 150 can be relocated, rearranged or reoriented within housing 152 while retaining equivalence in function according to the present invention.

While this invention has been described with reference to illustrative embodiments, this description is not intended to be construed in a limiting sense. Various modifications and combinations of the illustrative embodiments as well as other embodiments of the invention will be apparent to persons skilled in the art upon reference to the description. It is therefore intended that the appended claims encompass any such modifications or embodiments.

What is claimed is:

1. A portable, replaceable sensor cartridge for use with analytical measurements regarding one or more fluidic samples of interest, comprising:
   a housing having an opening, said opening allowing access to one or more electrically conductive contacts and one or more fluidic connectors disposed within said housing;
   a flow cell disposed within said housing and having one or more channels connected to said one or more fluidic connectors; and
   a fixed optic sensor disposed within said housing and having one or more optical components pre-positioned within said housing with respect to said flow cell, whereby the cartridge may be used with a portable host unit and may be replaced to permit field analysis of said one or more fluidic samples.

2. The cartridge as recited in claim 1 wherein said one or more electrically conductive contacts and one or more fluidic connectors are affixed to a platform.

3. The cartridge as recited in claim 2 wherein said one or more electrically conductive contacts are substantially flat contacts affixed to an edge of said platform.

4. The cartridge as recited in claim 2 wherein said one or more electrically conductive contacts are pins affixed to said platform.

5. The cartridge as recited in claim 2 wherein said platform is a printed circuit board recessed from said opening.

6. The cartridge as recited in claim 2 further comprising a temperature sensor coupled to said platform.

7. The cartridge as recited in claim 2 further comprising a thermal heating device coupled to said platform.

8. The cartridge as recited in claim 1 wherein said housing has one or more walls having a substantially rectangular shape.

9. The cartridge as recited in claim 1 wherein said housing has one or more walls having a substantially trapezoidal shape.

10. The cartridge as recited in claim 1 wherein said housing is opaque.

11. The cartridge as recited in claim 1 wherein said one or more electrically conductive contacts and said one or more fluidic connectors are substantially parallel.

12. The cartridge as recited in claim 1 wherein said fixed optic sensor comprises:
    a light source;
    a sensing surface mounted on a portion of said flow cell and in contact with one of said fluidic samples of interest and disposed at an angle to receive light transmitted from said light source; and
    a photodetector array for measuring intensity of a reflected component of said light.

13. The cartridge as recited in claim 1 wherein said fixed optic sensor is selected from the group consisting of, a surface plasmon resonance sensor, a critical angle sensor, and a fluorescence-based sensor.

14. The cartridge as recited in claim 1 wherein one or more external surfaces of said housing is textured with one or more contours.

15. The cartridge as recited in claim 1 wherein said one or more fluidic connectors is composed of teflon.

16. The cartridge as recited in claim 1 further comprising a receptacle connected to said one or more fluidic connectors, said receptacle containing therein one or more reagents for reacting with said one or more samples of interest.

17. The cartridge as recited in claim 1 further comprising one or more materials for calibration within said housing.

18. The cartridge as recited in claim 1 further comprising a digital signal processing unit within said housing and electrically connected to at least one of said one or more electrically conductive contacts.

19. The cartridge as recited in claim 1 further comprising a lid removably attached to said housing.

20. The cartridge as recited in claim 1 further comprising a waste unit within said housing and connected to said one or more fluidic connectors.

21. A portable, replaceable sensor cartridge for use with analytical measurements regarding one or more samples of interest, comprising:
    a housing having an opening, said opening allowing access to one or more electrically conductive contacts within said housing and at least one fluidic connector within said housing, with said contacts and at least one fluidic connector affixed to a printed circuit board within said housing and;
    a flow cell within said housing and having one or more channels connected to said one or more fluidic connectors;

a fixed optic sensor within said housing mechanically aligned to said flow cell;

a thermal heating device within said housing and electrically connected to said printed circuit board;

a temperature sensor within said housing and electrically connected to said printed circuit board;

a digital signal processing unit within said housing and electrically connected to at least one of said one or more electrically conductive contacts; and a waste unit within said housing and connected to said one or more fluidic connectors.

22. A method of optical sensing for use with analytical measurements regarding one or more samples of interest, said method comprising:

aligning a first set of at least two electrically conductive contacts and a first suction fluidic connector within a first housing;

connecting said first housing to a host analytical unit by establishing electrical connection between said first set of at least two electrically conductive contacts and said host analytical unit, and establishing fluidic connection between said first suction fluidic connector and said host analytical unit;

passing a fluid through a first intake fluidic connector into a first flow cell disposed within said housing;

sensing a fluid property with a first fixed optic sensor disposed within said housing;

removing said first housing together with said first set of electrically conductive contacts and said first suction and intake fluidic connectors, and said first flow cell, and said first fixed optic sensor disposed within said first housing; and replacing said first housing with a second housing, said second housing containing a second set of at least two electrically conductive contacts and second first suction and intake fluidic connectors, and a second flow cell, and a second fixed optic sensor.

* * * * *